US005183588A

United States Patent [19]
Salerno et al.

[11] Patent Number: 5,183,588
[45] Date of Patent: Feb. 2, 1993

[54] TERNARY SYSTEM BASED ON PERFLUORINATED ETHERS

[75] Inventors: Martine S. Salerno; Rémy Mounier; Bernard Breda, all of Neuilly sur Seine, France

[73] Assignee: Yves Saint Laurent Parfums, France

[21] Appl. No.: 503,980

[22] Filed: Apr. 4, 1990

[30] Foreign Application Priority Data

Oct. 13, 1989 [FR] France ................. 89 13426

[51] Int. Cl.$^5$ .............................. B01J 13/00
[52] U.S. Cl. ............................ 252/312; 252/309; 252/311; 514/63; 514/723; 514/844; 514/848; 514/938
[58] Field of Search ............... 514/63, 723, 844, 848, 514/938; 252/309, 311, 312

[56] References Cited

U.S. PATENT DOCUMENTS

| | | | |
|---|---|---|---|
| 4,013,475 | 3/1977 | Liebowitz et al. | 252/309 X |
| 4,122,029 | 10/1978 | Gee et al. | 252/309 |
| 4,311,695 | 1/1982 | Starch | 514/63 |
| 4,520,160 | 5/1985 | Brown | 524/765 |
| 4,532,632 | 7/1985 | Yamashita et al. | 372/50 |
| 4,780,245 | 10/1988 | Burke et al. | 252/312 |
| 4,797,273 | 1/1989 | Linn et al. | 252/311 X |
| 4,803,067 | 2/1989 | Brunetta et al. | 424/63 |
| 4,917,891 | 4/1990 | Kaufmann et al. | 514/63 X |
| 4,954,338 | 9/1990 | Mattox | 514/723 X |
| 4,960,764 | 10/1990 | Figueroa, Jr. et al. | 514/63 |
| 4,990,283 | 2/1991 | Visca et al. | 252/309 |

OTHER PUBLICATIONS

Bader, S. "Three-Phase Emulsions: Perfluoropolyether-Oil-Water" Cosmetics & Toiletries, vol. 101, No. 11, Nov. 1986.

Primary Examiner—Richard D. Lovering

[57] ABSTRACT

The invention consists in a ternary system.

The ternary system comprises three phases which are non-miscible with one another and consist of a phase of perfluorinated ethers, an aqueous phase and a phase of silicones comprising at least one straight-chain-silicone containing a glycol group and at least one cyclic-chain silicone containing a methyl group. These silicones can be of the dimethicone copolyol type and of the cyclomethicone type, respectively. And the aqueous phase preferably contains a hydrating agent, a co-emulsifier and an anti-bacterial preservative. The invention concerns in particular cosmetics.

4 Claims, No Drawings

TERNARY SYSTEM BASED ON PERFLUORINATED ETHERS

DESCRIPTION

1. Technical Field

The subject of the invention is a new ternary system based on a perfluorinated liquid and intended, in particular, for an application in the field of aesthetic and skin care cosmetics, in order to protect the skin and let it breathe.

2. Background of the Invention

Certainly, numerous systems and numerous cosmetic compositions for the treatment or beautifying of the skin have already been proposed; however, up to now these have proved, in a certain number of cases, to have little effectiveness in the sphere of the combined actions of hydration and protection of the skin, in combination with the necessary breathing of the latter.

However, combining these three essential principles, which are the hydration, the protection and the breathing of the skin, in one and the same system has proved difficult to obtain, taking account of the sometimes not readily compatible chemical characteristics inherent to each constituent of the system.

SUMMARY OF THE INVENTION

It is only after numerous and prolonged studies that the Applicant has been able to develop the new system of the invention, which system is a ternary system, comprising three phases which are non-miscible with one another and consist of:

a phase of perfluorinated ethers, an aqueous phase, and a phase of silicones comprising at least, on the one hand, a silicone having (a) straight chain(s) and possessing at least one glycol group and, on the other hand, a silicone having (a) cyclic chain(s) and possessing at least one methyl group.

In this way, the users, who are anxious in particular to lavish regular skin care on their faces, will have at their disposal a cosmetic product which has a non-greasy texture, which ensures a non-occlusive protection of their skin and with which the amount of perfluorinated ethers deposited on the skin will be able to be optimized by very rapid volatilization of the hydro-silicone part of the system.

BEST AND VARIOUS MODES FOR CARRYING OUT INVENTION

According to the invention, the perfluorinated ether preferably used is a perfluoropolymethylisopropyl ether.

Its chemical formula is as follows:

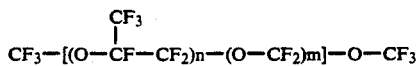

with n/m = 20 to 40.

This ether is also known under the simplified chemical name of perfluoropolyether and is manufactured, in particular, by the company "MONTEFLUOS" under the name "FOMBLIN HC" (registered trademark).

Advantageously, the perfluorinated ether chosen will have an average molecular mass oscillating between 1,500 and 6,600, with a vapour pressure of preferably less than or equal to about $10^{-7}$ mm Hg (which is about $131 \times 10^{-7}$ Pa, for a molecular mass of the order of 6,600) and in any case less than about $10^{-3}$ mm Hg, viz. about $131 \times 10^{-3}$ Pa (for a molecular mass of the order of 1,500). With regard to the surface tension taken at 20° C., this will be of the order of 20 to 25 mN/m.

Amongst the silicones provided for in the invention for combination with the selected perfluorinated ether, there will therefore be found, of necessity, at least one silicone having a straight chain or chains, provided as a surfactant and at least one silicone (preferably volatile) having a cyclic chain, intended to constitute a fluid base.

In the first category (straight-chain silicones), the silicones of the dimethicone copolyol type are very particularly appropriate, as are the cyclomethicones (CTFA designation) in the second category (cyclic silicone).

The dimethicone copolyols are copolymers of glycol which are soluble in water, in alcohol and in aqueous alcoholic systems In other words the compounds concerned are polymers of dimethylsiloxane comprising side chains of polyoxyethylene and/or of polyoxypropylene.

Their chemical formula is as follows:

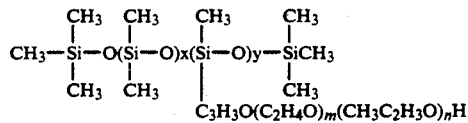

This type of silicone is marketed, in particular, by the company "DOW CORNING". With regard to the cyclomethicones, these are volatile dimethylpolysiloxane compounds which have the physical appearance of a fluid of low viscosity (of the order of 2.5 to 6 mm²/s at 25° C.) with a surface tension of the order of 18 to 21 mN/m (likewise at about 25° C.).

The chemical formula of the cyclomethicones is as follows:

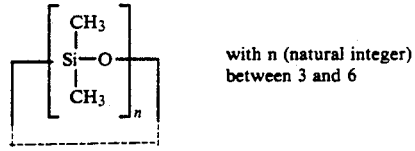

with n (natural integer) between 3 and 6

In the invention, this product will preferably be used essentially in its tetramer and/or pentamer form. However, it could also be conceivable to include it in its hexamer form in a smaller amount.

The cyclomethicones have been selected, in particular, because they have the advantage of acting efficiently as a skin cleaning agent, without producing a warming sensation.

As a fluid base or temporary carrier, they enable a product to be obtained which is easy to dilute and to extract and the diffusion of which is therefore straightforward.

A product of this type is marketed, in particular, by the company "DOW CORNING" under the name "DC 344" or "DC 345".

According to the invention, the various ingredients which have just been mentioned are preferably found in the final ternary system in the following concentrations:

perfluorinated ethers: between 0.1 and 5% by weight approximately, straight-chainsilicones (dimethiconecopolyol): between 0.1 and 5% approximately, and cyclic silicones (cyclomethicone): between 0.1 and 50% by weight approximately.

It should be noted that, if desired, the dimethicone copolyols and the cyclomethicones could, in part, be amalgamated within a single product of the self-emulsifiable volatile silicone type.

A silicone of this type is marketed, for example, by the company "DOW CORNING" under the name "DC 3225"

It has the appearance of a liquid which varies between transparency and a slightly opaque or turbid appearance.

In this product approximately 10% of dimethicone copolyol and approximately 90% of cyclomethicone are found.

Moreover, it will also be noted that the aqueous phase of the ternary system of the invention will advantageously comprise, as additives or adjuvants, a hydrating agent, a co-emulsifier (or adjunct emulsifier) consisting of an electrolyte as well as an anti-bacterial preservative.

The adjunct emulsifier could consist of sodium chloride or possibly even of potassium chloride.

With regard to the hydrating agents and anti-bacterial preservatives, they could be based on, respectively, glycerol and imidazolidinylurea, this latter constituent being manufactured, in particular, by the company "ADF chimie" under the name "GERMALL 115".

Two examples of implementation of a ternary system according to the invention will now be given by way of non-limiting illustration:

EXAMPLE 1

To obtain a system having the sought-after characteristics of the invention, the following ingredients, which thus are doses in % weight/weight, are mixed:

dimethicone copolyol: between 1 and 1.5% approximately, cyclomethicone of the tetramer type: between 14 and 23.5% approximately, cyclomethicone of the pentamer type between 5 and 10% approximately, perfluoropolymethylisopropyl ether: between 0.5 and 1% approximately, co-emulsifier (sodium chloride) of the order of 2%, hydrating agent (glycerol): between 3 and 5% approximately, anti-bacterial preservative: of the order of 0.3%, water, qs. 100.

EXAMPLE 2

The ingredients are now mixed in the following way, in % weight/weight:

combination of dimethicone copolyol (approximately 10%) and cyclomethicone of the tetramer type (approximately 90%) (DC 3225): approximately 10%, cyclomethicone of the tetramer type (DC 344): 5% approximately, cyclomethicone of the pentamer type (DC 345): 5% approximately, perfluorinated ether (FOMBLIN HC): 0.5% approximately, anti-bacterial preservative: 0.3% approximately, glycerol: 3% sodium chloride: 2% approximately, and distilled water: 74.2%.

We claim:

1. Emulsion comprising three phases non-miscible with one another, said phases consisting essentially of:
   a first phase of about 0.1 to 5% by weight of perfluorinated ether,
   a second phase comprising about 0.1 to 5% by weight of a straight-chain silicone containing a glycol group, as surfactant for forming said emulsion, and about 0.1 to 50% by weight of a cyclic-chain silicone containing a methyl group, as fluid base, and
   a third phase comprising about 3 to 5% by weight of hydrating agent, and water, qs 100.

2. Emulsion according to claim 1 wherein said straight-chain silicone is a dimethicone copolyol.

3. Emulsion according to claim 1 wherein said cyclic-chain silicone is a cyclomethicone.

4. Emulsion according to claim 1 wherein said ether is a perfluoropolymethylisopropyl ether.

* * * * *

UNITED STATES PATENT AND TRADEMARK OFFICE
CERTIFICATE OF CORRECTION

PATENT NO.  :   5,183,588
DATED       :   February 2, 1993
INVENTOR(S) :   Martine Seu Salerno, et al.

It is certified that error appears in the above-identified patent and that said Letters Patent is hereby corrected as shown below:

On the title page, in items [19] and [75] change "Salerno" to read --Seu Salerno--.

Column 2, line 20, after "systems" insert --,--.

Signed and Sealed this

Twenty-first Day of December, 1993

Attest:

BRUCE LEHMAN

*Attesting Officer*   *Commissioner of Patents and Trademarks*